United States Patent [19]

Evans et al.

[11] Patent Number: 5,263,972
[45] Date of Patent: Nov. 23, 1993

[54] SURGICAL HANDPIECE CHUCK AND BLADE

[75] Inventors: James A. Evans, Kalamazoo; Gary T. Kalinka, Grand Rapids, both of Mich.

[73] Assignee: Stryker Corporation, Kalamazoo, Mich.

[21] Appl. No.: 989,975

[22] Filed: Dec. 11, 1992

Related U.S. Application Data

[63] Continuation of Ser. No. 640,028, Jan. 11, 1991, abandoned.

[51] Int. Cl.$^5$ .................... A61B 17/32; A61B 17/14
[52] U.S. Cl. ............................ 606/176; 606/82; 30/351; 30/339
[58] Field of Search .................. 606/176–180, 606/167–172, 82, 132; 279/76, 96, 101, 102; 83/698; 30/335–339, 342, 351, 355, 166.3, 392, 393

[56] References Cited

U.S. PATENT DOCUMENTS

| | | |
|---|---|---|
| 44,823 | 10/1864 | Rpse . |
| D. 245,918 | 9/1977 | Shea . |
| D. 317,821 | 6/1991 | Aoyagi . |
| 436,804 | 9/1890 | Roberts . |
| 1,048,085 | 12/1912 | MacFarland . |
| 1,064,493 | 6/1913 | Kropat . |
| 1,125,234 | 1/1915 | White . |
| 1,413,101 | 4/1922 | Cushing . |
| 1,448,305 | 3/1923 | Langbein . |
| 1,495,675 | 5/1924 | Colt . |
| 1,940,855 | 12/1933 | Friedman . |
| 2,557,364 | 6/1951 | Treace . |
| 2,604,130 | 7/1952 | Derby . |
| 2,649,838 | 8/1953 | Krause et al. . |
| 2,854,981 | 10/1958 | Morrison . |
| 3,103,069 | 9/1963 | Gary . |
| 3,542,097 | 11/1970 | Dudek . |
| 3,554,197 | 1/1971 | Dobbie . |
| 3,678,934 | 7/1972 | Warfield et al. . |
| 3,750,283 | 8/1973 | Hoffman . |
| 3,823,473 | 7/1974 | Hoffman . |
| 3,852,881 | 12/1974 | Treace . |
| 3,863,339 | 2/1975 | Reaney et al. . |
| 3,901,117 | 8/1975 | Hoffman . |
| 3,905,105 | 9/1975 | Tuke . |
| 3,905,374 | 9/1975 | Winter . |
| 3,927,893 | 12/1975 | Dillon et al. . |
| 3,943,934 | 3/1976 | Bent . |
| 3,952,412 | 4/1976 | Rhodes . |
| 3,964,163 | 6/1976 | Russo .................... 30/342 |
| 3,974,868 | 8/1976 | Derbyshire . |
| 4,008,720 | 2/1977 | Brinckmann et al. . |
| 4,020,555 | 5/1977 | Hedrick . |
| 4,032,747 | 6/1977 | Kunz . |
| 4,064,871 | 12/1977 | Reno . |
| 4,106,181 | 8/1978 | Mattchen . |
| 4,233,737 | 11/1980 | Poehlmann . |
| 4,252,121 | 2/1981 | Arnegger . |
| 4,386,609 | 6/1983 | Mongeon . |
| 4,470,196 | 9/1984 | Hoffman . |
| 4,528,753 | 7/1985 | Kuhlmann et al. . |
| 4,584,999 | 4/1986 | Arnegger . |
| 4,617,930 | 10/1986 | Saunders . |
| 4,637,391 | 1/1987 | Schlein . |
| 4,646,440 | 3/1987 | Decker . |
| 4,648,182 | 3/1987 | Hoffman . |
| 4,694,542 | 9/1977 | Koppe . |
| 4,711,030 | 12/1987 | Ruston . |
| 4,730,952 | 3/1988 | Wiley . |
| 4,736,742 | 4/1988 | Alexson et al. . |
| 4,739,557 | 4/1988 | Wagner . |
| 4,768,504 | 9/1988 | Ender . |
| 4,783,886 | 11/1988 | Koppe . |
| 4,819,334 | 4/1989 | Mongeon . |
| 4,891,884 | 1/1990 | Torbet . |
| 4,899,443 | 2/1990 | Beermann . |
| 4,920,646 | 5/1990 | Grant . |
| 5,122,142 | 6/1992 | Pascaloff . |

OTHER PUBLICATIONS

Copy of Stryker Maintenance Manual entitled "System II OrthoPower 90 Battery Powered Surgical Instruments"—for Use With: 298-92, 94, 96, 98. (Stryker Surgical Brochure 298-92-16 REV (Mar. 1986).
Sketch.
Stryker Surgical brochure 298-92-16 (Mar. 1986).

*Primary Examiner*—C. Fred Rosenbaum
*Assistant Examiner*—Ronald K. Stright, Jr.
*Attorney, Agent, or Firm*—Flynn, Thiel, Boutell & Tanis

[57] ABSTRACT

A blade with a cutting part on one edge portion thereof has a remote end fixed in a chuck by pushing same end-wise into a slot in the chuck through a series of positions, namely (1) drop-out, (2) safety locked-in and (3) fully inserted locked-in.

16 Claims, 4 Drawing Sheets

SURGICAL HANDPIECE CHUCK AND BLADE

This application is a continuation of U.S. Ser. No. 07/640 028, filed Jan. 11, 1991 now abandoned.

FIELD OF THE INVENTION

This invention relates to a cooperating chuck and removable blade for surgical tools, particularly including powered surgical oscillating and sagittal saws.

BACKGROUND OF THE INVENTION

In a prior sagittal saw marketed by the Assignee of the present invention, a powered surgical handpiece carries a sagittal saw chuck capable of removably chucking various blades on a one-at-a-time basis. Each of the prior blades has a widened, rounded base perforated by a coaxially located, circumferentially spaced, pattern of identical through holes and a central, rear opening slit. The prior chuck has a bottom member having a pattern of upstanding pins located to enter the through holes in the blade base. A chuck top member has a center post depending through a central opening of the bottom member and spring biased down to pull the top member down onto the top member's upstanding pins.

To load a blade into the chuck requires gripping of three members as follows.

1. The handpiece is fixedly supported.
2. The resiliently downwardly urged top member is pulled upward from the bottom member pins to open the chuck.
3. The blade base is inserted into the now open chuck with its rear opening slit receiving the top member post.

Chucking of a blade requires that the blade be moved in several directions with respect to the handpiece. More particularly, the blade must be inserted horizontally into the open chuck, then the blade must be pivoted horizontally until its holes align with the upstanding bottom member pins, and then the blade base is dropped onto the chuck bottom member.

Then the spring biased chuck top member can be dropped onto the bottom member pins which then enter into a corresponding pattern of recesses in the bottom of the top member which in turn is pulled down to press down on the base of the blade. In this manner, the blade is locked fixedly with respect to the chuck. Removal of a blade from the chuck involves a reversal of the aforementioned steps.

Although the above-described prior chuck and tool have worked well for a substantial period of time, and have been found satisfactory by surgeons, nevertheless, the present Applicant has noted certain drawbacks of the above-discussed prior system, which drawbacks the present invention is intended to cure.

Accordingly, the objects and purposes of the present invention include provision of a surgical tool chuck and blade structure in which full insertion of blade into chuck can be done easily with only two (rather than three) hands; in which a blade is chucked merely by pushing it longitudinally into the chuck while pushing a locking element on the chuck; in which the blade is either obviously insufficiently inserted or is positively locked against escape from the chuck; in which significant insertion of the blade into the chuck requires manual pushing of a locking element; in which such insufficient insertion is made obvious by a number of observables including short insertion distance before insertion is positively blocked, virtually no blade retention force, free pivoting of the blade from side to side and up and down (roll and pitch) with respect to the chuck, and dropping of the blade out of the chuck upon almost any movement of the chuck or handpiece; in which positive locking of the blade in the chuck is present for almost the entire longitudinal insertion of the blade base into the chuck; in which such positive locking prevents the blade from accidentally being removed from the chuck even when the blade is not fully inserted into the chuck; in which the possibility of accidental release of the locking element by careless handling of the chuck or handpiece is minimized; in which a blade can simply be dropped out of its fully inserted and positively locked position in the chuck by one handed gripping of the chuck in a way to push the locking element; in which the blade tends to be seated more firmly in the chuck during cutting; in which locking of the blade in the chuck and prevention of rocking of the blade in the chuck are carried out by different portions of the chuck acting on the blade; in which the chuck can be made more compact than the prior chuck above described, in which the chuck and blade are of simple relatively inexpensive construction, in which blades of a range of differing thicknesses can be inserted in the chuck without any manipulation of the chuck to compensate for differences in thickness and wherein the chuck automatically compensates for differences in thicknesses of blades; in which the number of parts is substantially reduced; in which the blade receiving portion of the chuck is constructible in two facing pieces which can be easily machined and thereafter permanently fixed together as by electron beam welding, and in which the insertion and removal of a blade with respect to the chuck can be carried out by persons without special training and under the adverse conditions often encountered in surgery.

Further objects and purposes of the invention will be apparent to persons familiar with an apparatus of this kind upon reading the following description and upon inspection of the accompanying drawings.

SUMMARY OF THE INVENTION

A blade with cutting means on one edge portion thereof has a remote end fixed in a chuck by pushing same end-wise into a slot in the chuck through a series of positions, namely (1) drop-out, (2) safety locked-in and (3) fully inserted locked-in.

DETAILED DESCRIPTION

Figure 1:
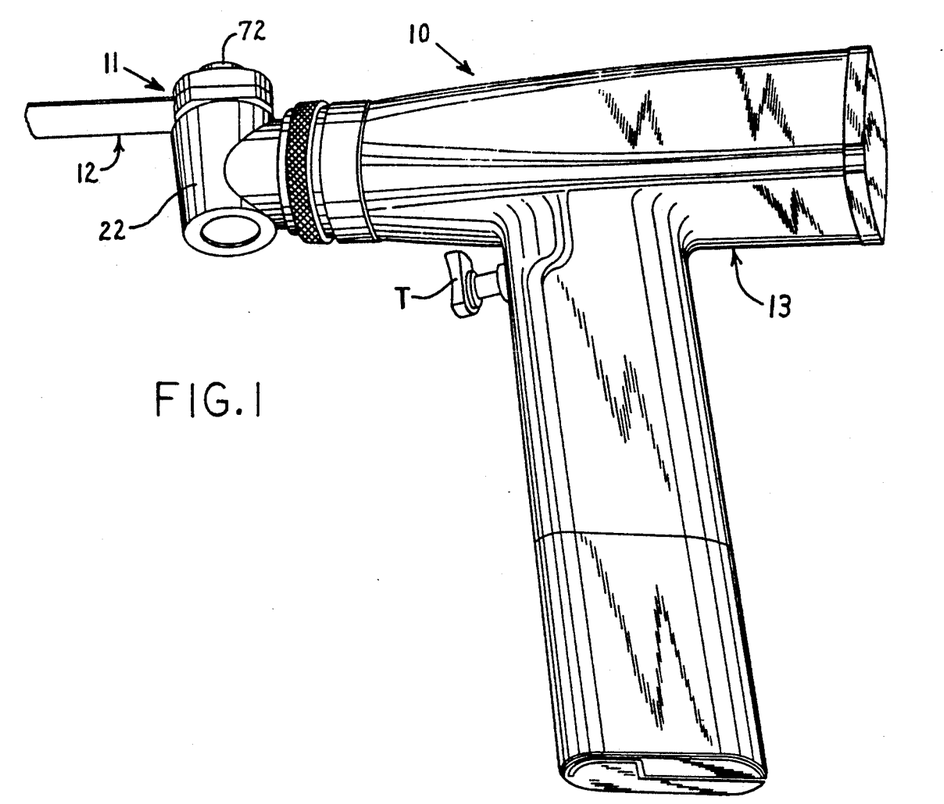
FIG. 1 is a pictorial view of a surgical handpiece of a kind usable as a powered sagittal or oscillating saw, and including a chuck and blade construction embodying the present invention.

FIG. 1 discloses a powered surgical handpiece 10 which provides a typical environment for a chuck 11 and blade 12 more specifically embodying the invention. The handpiece 10 may be of the type including a housing 13 enclosing a motorized drive assembly 14 of any convenient type schematically indicated in FIG. 2. The motorized drive assembly 14 typically includes a drive motor M powered from a power source P through a switch S in turn actuated by a trigger T. In one embodiment according to the invention, the power source P is electric, although other energy sources (for example, compressed air) are contemplated.

Figure 2:
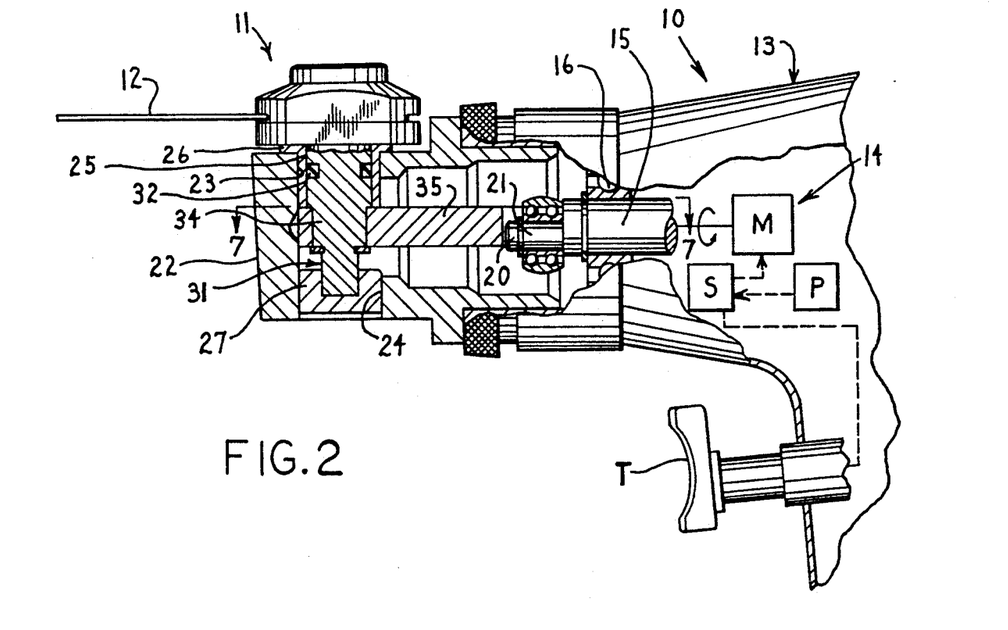
FIG. 2 is an enlarged central cross-sectional view, in elevation, of a fragment of FIG. 1 handpiece showing a chuck and blade embodying the invention and a drive structure therefor, as supported in a forward portion of the handpiece of FIG. 1.

Although oscillating motion about a vertical axis (in FIG. 2) may be imparted to the chuck 11 by any convenient means, in the example shown in FIG. 2, the motor M drives a rotatable shaft 15, rotatably supported by suitable bearings, as at 16, supported by the housing 13. The forward end of the shaft 15 carries an axially extending but eccentrically located drive pin 20 fixed thereon and in turn carrying a bearing 21 axially fixed thereon.

Fixed to and extending forward from the housing 13 is a hollow extension 22, which is blind at its forward end but has coaxially spaced top and bottom through bores 23 and 24. An axial sleeve 25 is press fitted down into the top bore 23 and has a radial flange 26 resting atop the extension 22. A blind bottomed bushing 27 is press fitted up into the bottom bore 24 coaxially of the sleeve 25.

The chuck 11 includes a central depending shaft 31 supported for pivotal movement about its longitudinal axis (vertical in FIG. 2) by the sleeve 25 and bushing 27. In the embodiment shown, the shaft 31 has maximum and minimum diameter portions at the top and bottom thereof which are respectively rotatably supported by the sleeve 25 and bushing 27. The maximum diameter portion of the shaft is annularly grooved to receive an O-ring 32 (FIG. 2) which seals against the sleeve 25. The O-ring 32 and blind bushing 27 seal the interior of the housing extension 22.

Figures 6, 6A, 7:
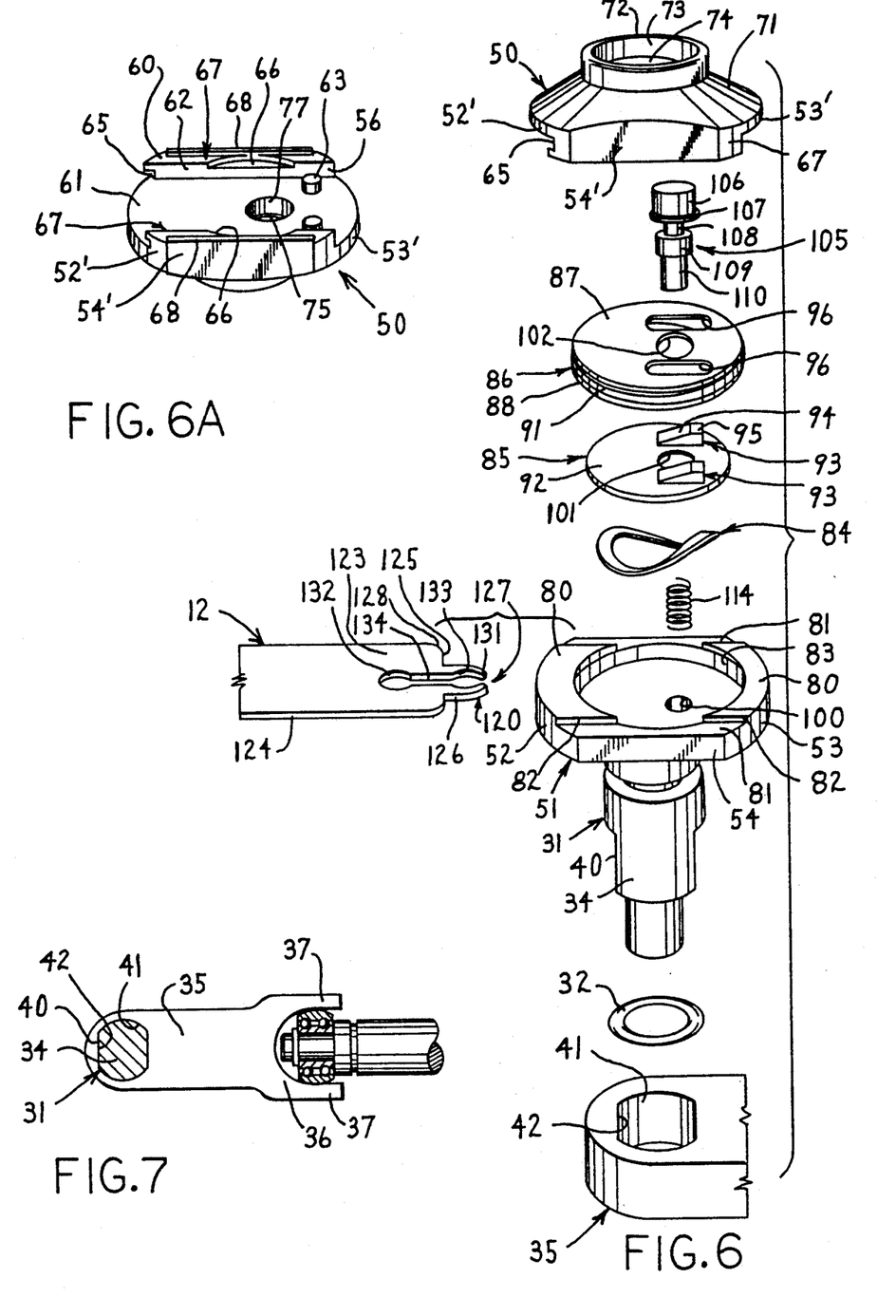
FIG. 6 is an exploded pictorial view of the FIG. 1 chuck.
FIG. 6A is a pictorial view of the chuck top member of FIG. 6 but oriented upside down (as if rotated from FIG. 6 about a horizontal axis in the plane of the page).
FIG. 7 is a fragmentary sectional view taken substantially on the line 7—7 of FIG. 2.

An intermediate portion 34 of the shaft 31 disposed just below the sleeve 25 has fixed thereto the forward (leftward) end of a link 35. The rearward (rightward) end of the link 35 forms a fork 36 (FIG. 7). The fork 36 has a laterally spaced pair of rearwardly extending tines 37. The tines 37 snugly receive laterally therebetween the outer race of the bearing 21 carried by the eccentric drive pin 20. The opposed surfaces of the tines 37 are vertical and extend above and below the central axis of the rotating shaft 15 sufficiently to maintain contact with the outer race of the bearing 21 as it moves on a vertical plane, through the circular orbit of the eccentric pin 20, as the pin orbits in response to rotation of the shaft 15. Thus, as the shaft 15 rotates and the eccentric pin 20 and surrounding bearing 21 orbit, the bearing 21 moves up and down along the opposed faces of the tines 37 in response to the vertical component of the orbit and pivotally rocks the fork 36 and link 35 and chuck 11 about the vertical axis of the chuck shaft 31 in response to the horizontal component of the orbit. Such rocking thus is in a horizontal plane and more specifically in a direction into and out of the page in FIG. 2 and is in the plane of the page in FIG. 3. Such pivotal rocking of the chuck 11, causes a blade 12 carried by the chuck 11 to oscillate horizontally.

To assure that the link 35 positively oscillates the chuck shaft 31, the chuck shaft 31 (FIG. 7) in its intermediate portion 34 may be provided with oppositely facing flats 40. The forward end of the link 35 receives the intermediate portion 34 of the shaft 31 in a broached, vertical, through hole 41 provided with corresponding flats 42. The hole 41 in the forward end of the link 35 is thus sized and shaped to receive the intermediate portion 34 of the shaft 31 vertically therethrough in fixed, press fitted, and positive driving relation.

To the extent above described, the apparatus is conventional and is disclosed as a typical environment for the chuck 11 and blade 12 more specifically embodying the invention.

It will be noted that variations on the above-described environmental apparatus are contemplated. For example, the desired oscillating motion may be imparted to the chuck 11 and blade 12 by other means than the link 35 and orbiting eccentric 20 discussed above, although the disclosed link and eccentric structure discussed above provide an effective yet economical structure for imparting the desired oscillatory movement to the chuck 11 and blade 12.

Figure 4:
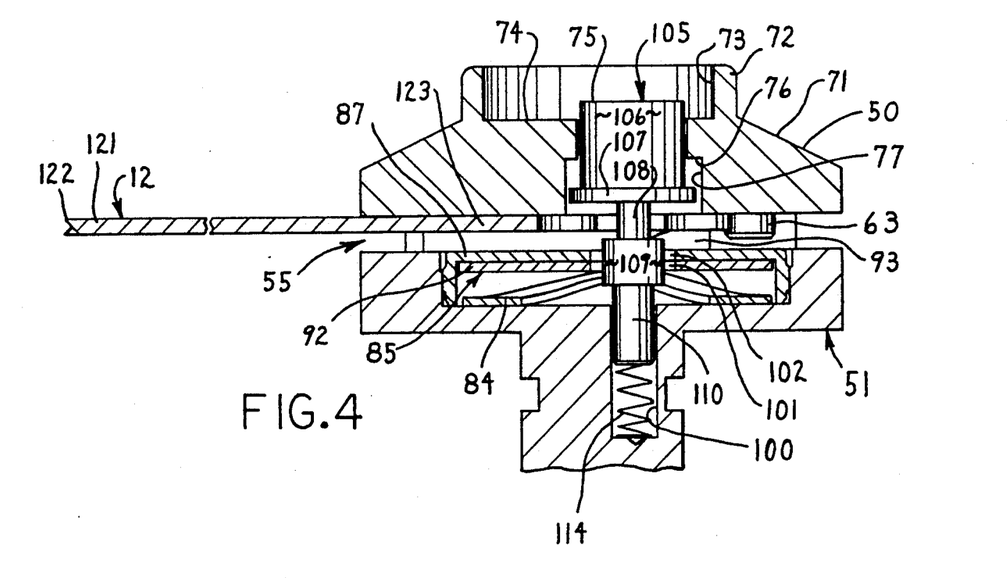
FIGS. 4 and 4A are enlarged central cross-sectional views substantially taken on the line 4A—4A of FIG. 3 and respectively showing partly and fully inserted blade positions corresponding to FIGS. 5D and 5E.

Turning now to structure more directly embodying the invention, the chuck 11 comprises facing top and bottom casing members 50 and 51 (FIGS. 4 and 6). The bottom casing member 51 is fixed centrally atop, and preferably integral with, the shaft 31. In the embodiment shown, the casing members 50 and 51 have the same outline in top plan view. In the bottom member 51, the forward and rearward ends 52 and 53 (FIG. 6) respectively are convexly rounded and connected by longitudinal sides 54 which are flatted and parallel. As seen at 52'-54', the top member 50 is similar.

The chuck 11 has a horizontal, longitudinal, preferably rectangular cross section, forward opening slot 55 (FIG. 4) in which the rear end portion of the blade 12 is received as hereafter discussed. The slot 55 is formed by a corresponding longitudinal, rectangular cross section groove 56 (FIG. 6A) extending centrally in the bottom face 60 of the top member 50. The groove 56 opens through the front end 52' of the top member 50. The groove 56 may open through the rear end 53' for convenience in machining. The groove 56 has side walls 62 connected by a central flat 61 depressed from but parallel to the plane of the bottom face 60. The side walls 62 of the groove 56 are parallel and extend forwardly/rearwardly of the top chuck member 50 and here are perpendicular to the groove central flat 61 and the bottom face 60.

Figure 4A:
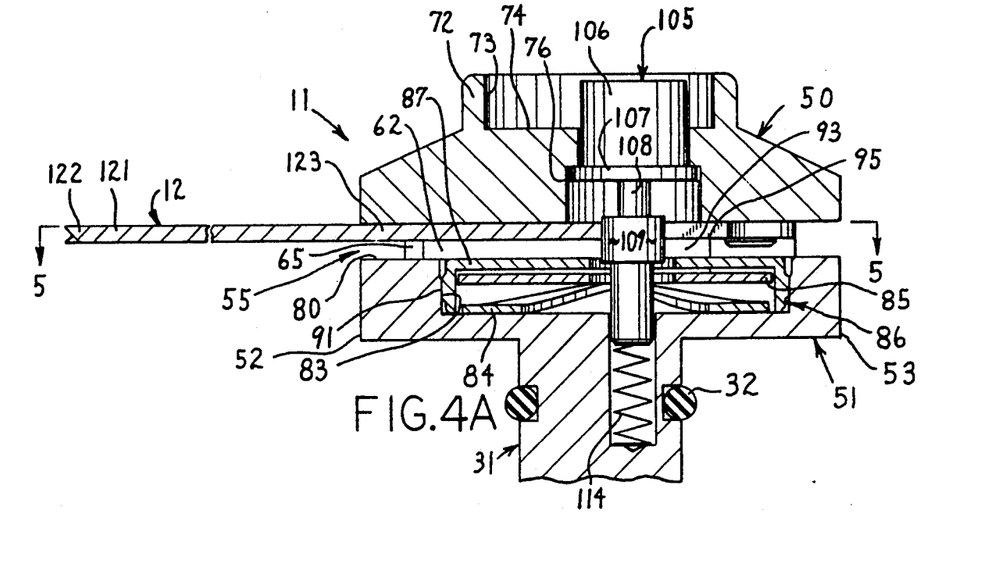

Two projections, here pins 63 (FIG. 6A), fixedly depend from the central flat 61 near the rear end 53' of top member 50 and are spaced between the groove side walls 62 and the front rear center line of the top member 50. The pins 63 may readily be fixed to the top member 50 by press fitting into vertical blind holes (not shown) in the top member 50. The pins 63 extend about half the depth of the slot 55 (FIG. 4A).

The front edges 65 (FIG. 6A) of the side walls 62 of the groove 56 in the top member 50 are rounded or bevelled to facilitate entry of the blade 12 into the slot 55 defined by the groove 56 and to reduce subsequent stress of the blade 12 bearing thereupon. The bottom face 60 of the top member 50 has laterally opposed, semicircular notches 66 which open toward each other across the groove 56, through the respective groove side walls 62, and extend vertically partway the depth of the groove side walls 62. The laterally opposed notches 66 are here offset slightly to the rear along the groove 56 but are forward of the pins 63. The notches 66 define diametrally opposed chordal portions of an imaginary circle laterally centered on the top member 50.

The groove 56 may be thought to define a laterally opposed pair of side bulkheads 67 (FIG. 6A). The side bulkheads 67 thus are flush with the sides 54' of the top member 50 and define the bottom face 60 and side walls 62. The bevels 65 and notches 66 are in the side bulkheads 67.

In the embodiment shown, a sacrificial ridge 68 (FIG. 6A) depends from the bulkheads 67 on each side of the top member 50. Each ridge 68 is flush with the corresponding outer side 54' of the top member 50 and extends the front-rear length thereof. The ridges 68 here extend along the outside perimeter of the respective notches 66. The ridges 68 are here of substantially rectangular cross section. The cross section of the ridges 68 is very small compared to the cross section of the corresponding bulkheads 67. The ridges 68 are sized to melt down during electron beam welding of the top member 50 to the bottom member 51 to weld the same together face to face.

In the embodiment shown, the top 71 (FIG. 6) of the top member 50 tapers upward toward an upstanding, cylindrical, circular fence 72 (FIG. 6). The fence 72 surrounds an upward facing recess 73 having a flat bottom 74 (FIGS. 6 and 4). In the embodiment shown, the fence 72 is substantially centered atop the top member 50. A vertical hole 75 extends down through the top member 50, as seen in FIGS. 4 and 6A. The hole 75 is centered laterally between the bulkheads 67 but is offset somewhat rearwardly on the top member 50. The hole 75 indeed has its center somewhat rearward of the center of the notches 66 but forward of the pins 63.

The bottom portion of the hole 75 is enlarged in diameter to form a downward facing step 76 (FIG. 4) and a corresponding downward opening recess 77. The recess 77 opens through the central flat 61 of the top member 50. The top of the hole 75 opens through the flat bottom 74 of the upward facing recess 73 bounded by the fence 72 and is offset rearwardly in the recess 73.

Figure 9:
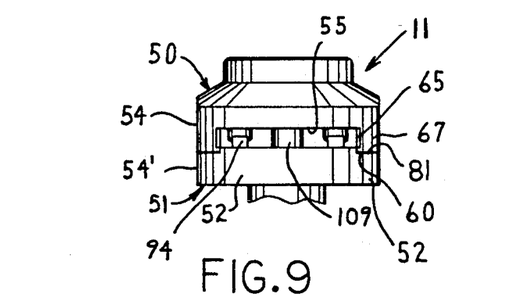
FIG. 9 is a front elevational view of the chuck of FIG. 8, with no blade inserted.

The bottom member 51 has a top face 80 (FIG. 6) in a plane perpendicular to the longitudinal axis of the shaft 31, and hence oriented horizontally in FIG. 6. The top face 80 is laterally flanked by coplanar flats 81 which extend forward-rearward along the respective sides 54 of the bottom member 51. The flats 81 are offset downward from the plane of the top face 80 by laterally outward facing steps 82. The height of the steps 82 is less than the height of the side walls 62 of the bulkheads 67 of the top member 50, by an amount corresponding to the height of the blade receiving slot 65 (FIG. 9) of the chuck 11. The flats 81 are horizontally sized to snugly receive thereon the respective bulkheads 67 of the top member 50 as seen for example in FIG. 9. This prevents lateral movement of the top member 50 with respect to the bottom member 51 during electron beam welding together of the members 50 and 51. During electron beam welding, the meltdown of the ridges 68 on the top member 50 results in face-to-face engagement of the bottom face 60 (the bottom of the bulkheads 67) of the top member 50 with the upward facing flats 81 of the bottom member 51 as seen in FIG. 9.

A shallow, circular, cylindrical recess 83 is sunk in the top face 80 of the bottom member 51 and is slightly offset to the rear therein as seen in FIG. 6. The laterally opposed, semicircular notches 66 in the underside of the bulkheads 67 of the top member 50 overlie the laterally opposed portions of the recess 83 in the bottom member 51, which portions extend laterally into the flats 81 of the bottom member 51. Thus, the semicircular notches 66 accommodate laterally opposed top portions of the shoe cover 86, in the assembled chuck 11. The recess 83 and flats 81 leave the top face 80 in the form of two semi-circular upward facing surfaces of which the front is somewhat wider in a front-rear direction than the rear.

The recess 83 contains, in ascending order, a compression spring in the form of a resilient wave washer 84 (FIGS. 4A and 6), a disk-like shoe 85, and an inverted cup-shaped shoe cover 86.

The cup-shaped shoe cover 86 has a flat top end wall 87 (FIGS. 6) of circular shape from which depends an annular peripheral wall 88. The height of the shoe cover 86 corresponds to the depth of the recess 83. The shoe cover 86 is press fitted fixedly into the recess 83, its top wall 87 flush with the top face 80 of the bottom member 51. The bottom of the peripheral wall 88 may rest on the bottom of the recess 83. To facilitate press fitting of the shoe cover 86 into the recess 83, the peripheral wall 88 of the shoe cover is on its outer face provided with an axially and radially narrow annular ridge 91 which snugly engages the side wall of the recess 83 in press fit relation therewith. The shoe cover 86 and the bottom of the recess 83 define a chamber in which the wave washer 84 and the overlying shoe 85 are housed in radial clearance, vertically movable relation. The wave washer 84 resiliently presses the shoe 85 upward against the top end wall 87 of the shoe cover 86 as shown in FIG. 4.

The shoe 85 comprises a circular disk 92 (FIG. 6) fixedly supporting a laterally spaced pair of ramps 93. The ramps 93 are offset somewhat to the rear on the upper face of the disk 92 and are laterally spaced on opposite sides of the front-rear centerline of the disk. The ramps 93 are preferably identical and each has a relatively shallow, forward facing and downward extending slope 94 which occupies most of the length of the ramp 93, and a relatively short, horizontal top 95.

Figure 4B:
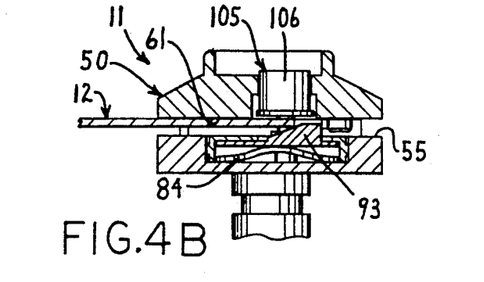
FIGS. 4B and 4C are enlarged central cross-sectional views substantially taken on the line 4B—4B of FIG. 5D and line 4C—4C of FIG. 5E respectively.

The top wall 87 of the shoe cover 86 is pierced by laterally spaced, forward-rearward extended slots 96 (FIG. 6) sized and located to allow the ramps 93 to extend upward therethrough with sufficient horizontal clearance as to allow the disk 92 of the shoe 85 to move up and down within the shoe cover 86. The outside diameter of the disk 92 is slightly less than the inside diameter of the shoe cover peripheral wall 88, so as not to restrict such up and down movement. Different vertical positions of the shoe 85 under the top 87 of the shoe cover 86 are seen for example in FIGS. 4 and 4A, and in FIGS. 4B and 4C. In their uppermost position (for example in FIG. 4B), the ramps 93 extend almost up to the central flat 61 of the upper member 50, being spaced therefrom by less than the thickness of the thinnest blade 12 intended to be chucked in the chuck 11.

Figure 5A:
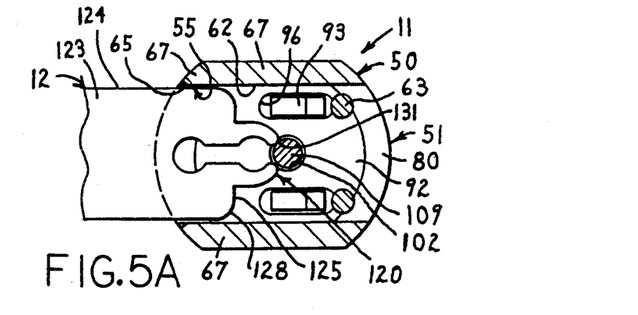
FIGS. 5A-5E are corresponding reduced cross-sectional views substantially taken on the line 5—5 of FIG. 4A with the blade at successive positions of insertion in the chuck.

As seen in FIG. 5A, the depending pins 63 of the top member 50 are each forward-rearward aligned with a corresponding ramp 93 and slot 96.

The bottom of the recess 83 (FIGS. 4 and 6), the disk 92, and the shoe cover top wall 87 have coaxially aligned holes 100, 101 and 102 respectively. The holes 100-102 are offset somewhat rearward on their respective members and are all in coaxial alignment with the hole 75 and recess 77 in the top member 50. In the embodiment shown, the holes 101 and 102 are of diameter less than the hole 75 but of diameter greater than the hole 100. The holes 101 and 102 are through holes. The hole 100, although axially much longer (deeper) than the holes 101 and 102, is blind as seen in FIG. 4.

The holes 100-102 are offset somewhat rearward of the central axis of the shaft 31, and are located laterally between the ramps 93, slots 96 laterally and forward of the pins 63.

A locking spindle 105 (FIGS. 4 and 6) comprises, in sequence downwardly, an enlarged cylindrical head 106, a radially outward extending flange 107, an unlocking segment 108 of substantially reduced diameter, a locking segment 109 of intermediate diameter, and a shank 110. The shank 110 is here of diameter between that of the segments 108 and 109. The elements 106-110 are coaxial and preferably are all cylindrical and of circular cross section.

A coil compression spring 114 is received with clearance in the blind hole 100 and can expand and be compressed axially in such hole 100. The shank 110 is snugly but vertically slidably received in the hole 100 atop the spring 114. The holes 101 and 102 in the shoe 85 and shoe cover 86 are sized to receive loosely therethrough the segments 108 and 109 and the shank 110 of the locking spindle 105, as seen in FIG. 4. The head 106 and flange 107 of the locking spindle 105 substantially exceed the diameter of the holes 101 and 102. However, the head 106 and flange 107 are of diameter to be snugly but vertically slidably received in the hole 75 and recess 77 in the top member 50.

The flange 107 (FIG. 4A) is of diameter larger than the hole 75 so as to coact with the step 76 to prevent the locking spindle 105 from escaping upward through the top member 50, despite the upward urging of the partially compressed compression spring 114. In other words, the flange 107 traps the locking spindle 105 within the chuck 11. In particular, the locking spindle 105 is free to move up and down in the chuck 11 until the flange 107 collides with either the step 76 or the top end wall 87 of the shoe cover 86 (assuming no blade 12 is in place in the chuck).

In its uppermost position, the top of the spindle head 106 is spaced slightly below the top of the fence 72 (FIG. 4A). In this uppermost position, the top of the locking spindle head 106 spaced well above the bottom 74 of the recess 73 defined by the fence 72. In this way, the fence 72 and spindle head 106 cooperate to allow intended pushing down of the locking spindle 105, from its FIG. 4A position toward its FIG. 4 position, by use of a thumb or finger, but to prevent accidental (unintended) pushing down of the locking spindle 105 when the palm of the user is pressed against the top of the chuck 11, as when a surgical assistant passes the handpiece 10 to a surgeon while grasping it by means of the chuck.

The blades 12 (FIG. 3) to be used with the chuck 11 include a cutting portion 121 remote from the chuck and typically being formed as a set of cutting teeth 122. Further, the blades 12 each have a mounting portion 123 (FIGS. 4 and 5A) to be received in the chuck 11. While the blades useable with the chuck 11 may take a variety of forms, in accord with their particular cutting task, and may thus differ in their size and shape outside the mounting portion 123 thereof, and indeed may even differ in the thickness of the mounting portion 123 thereof, up to a maximum thickness which can be received in the chuck slot 55, a typical blade 12 is here shown for purposes of illustration. The typical blade 12 here shown is of flat metal (preferably the relatively hard grade of stainless steel typically used for surgical saw blades), and is of elongate, generally rectangular plan, with the teeth 122 at the forward end thereof and the mounting portion 123 at the rearward end thereof.

Figure 5B:
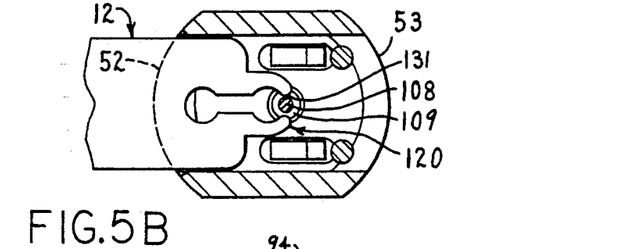
Figure 5C:
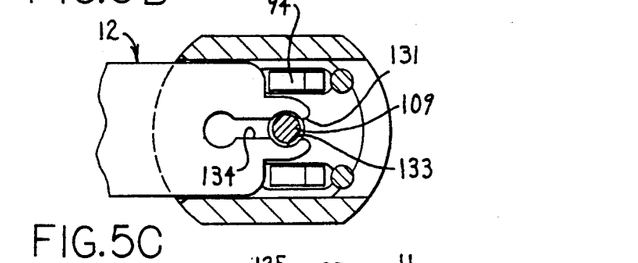
Figure 5D:
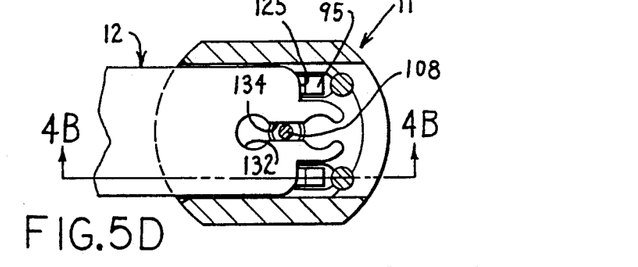
Figure 5E:
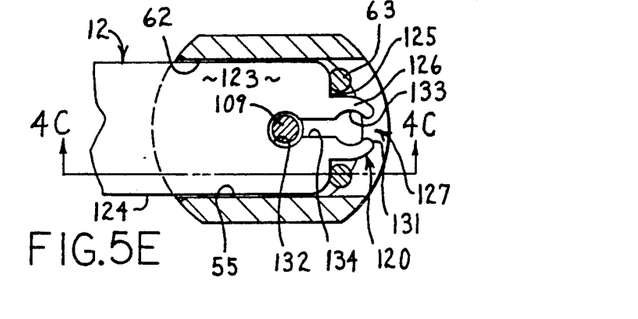

The mounting portion 123 of the blade 12 comprises parallel opposed side edges 124 (FIG. 5A) snugly but slidably received between the side walls 62 of the slot 55. It is desirable that, as seen in FIG. 5E, the width of the blade mounting portion 123 is very nearly as great as the width of the slot 55 into which it is rearwardly slidably receivable. It is also desirable that the side edges 124 be long, e.g. nearly as long as the slot 55. This snug but slidable contact over most of the length of the groove 56 prevents rocking of the blade 12 from side to side with respect to the chuck 11 during cutting, so that when the chuck 11 oscillates, horizontally, such motion is imparted to a blade 12 therein.

The rear end 125 of the blade meets the side edges 124 at rounded or beveled corners 128 (FIG. 5A) to ease insertion of the blade 12 rearwardly into the slot 55.

Integral with and extending rearward from the rear end 125 of the blade is rounded end nose 120 (FIGS. 5E and 6) centrally divided into a pair of laterally closespaced tines 126 spaced by a narrow central slit 127. The nose 120 is narrow compared to the width of the blade 12. The nose 120 is longitudinally short compared to the width of the mounting portion 93 of the blade 12. The slit 127 is of dumbbell shape, having an opposed pair of front notches and an opposed pair of rear notches here defined by respective circular front and rear parts 132 and 133, connected by a laterally narrower but longer neck 134. The open rear mouth 131 of the slit 127 is bevelled or rounded. The mouth 131 and neck 134 are sized to pass therethrough the unlocking segment 108 of the spindle 105 but not the locking segment 108, as seen in FIGS. 5B and 5D. Conversely, the circular parts 132 and 133 are sized to snugly receive the locking spindle 109 of the spindle 105 as seen in FIGS. 5C and 5E therein.

OPERATION

The blades 12 may be formed conventionally from stainless steel sheet stock, for example, by stamping and setting and hardening the teeth.

The parts of the chuck 11 are machined, or otherwise formed in any convenient manner, preferably from stainless steel sock. The resulting chuck parts shown in FIG. 6 are then assembled. More particularly, and most easily with the parts turned upside down, the shoe 85 and wave washer 84 are placed in the open end of the shoe cover 86 with the ramps 93 extending through the slots 96. The thus loaded shoe cover 86 has its peripheral wall 88 press fitted into the recess 83 in the bottom member 51. This traps the wave washer and shoe 85 between the top end wall 87 of the shoe cover and the bottom of the recess 83 in the bottom member 51, as seen for example in FIG. 4. The resultant assembly can then be turned to the upright position shown in the drawings.

The coil spring 114 and the shank 110 of the spindle 105 can then be dropped down through the holes 101 and 102 (FIG. 4) and into the blind hole 100 in the bottom member 51. The chuck top member 50, with its fixed dependent pins 63, can then be placed atop the bottom member 51, while the hole 75 and recess 77 in the top member 51 respectively receive the head 106 and flange 107 of the spindle 105. With the top and bottom members 50 and 51 properly aligned, electron beam welding melts down the sacrificial ridges 68 in the top member 50 to weld the top member bulkheads 67 atop the bottom member flats 81 (FIGS. 6 and 9). This completes assembly of the chuck 11 in its condition of FIGS. 4A and 9). The top and bottom members 50 and 51 thus become a one-piece unit and define the rectangular cross section, blade receiving slot 55 (FIGS. 4 and 9).

The assembled chuck 11 can then be pivotally mounted on the extension 22 on the front end of the handpiece 10. More particularly, with the sleeve 25 (FIG. 2) fixed in the top bore 23 of the extension 22, the chuck shaft 31 is slid downward through the sleeve 45 until the chuck bottom member 51 seats firmly on the flange 26 and the intermediate portion 34 is located below the sleeve 25.

The link 35 is predisposed in the hollow interior of the extension 22. As the chuck 11 is moved downward toward the extension 22 and the chuck shaft 31 slides downward through the sleeve 25, the lower end of the shaft 31 is guided through the hole 41 in the forward end of the link 35. A conventional tubular mandrel not shown can be inserted upward through the open bottom bore 24 to receive the bottom end of the shaft 31 and press the forward end of the link 35 onto the intermediate portion 34 of the shaft 31, with the flats 42 and 40 of the link 35 and shaft intermediate portion 34 opposed. The mandrel can then be withdrawn and the blind bushing 27 pressed upward into the bore 24 and over the bottom portion of the shaft.

It is desirable that foreign material from outside the handpiece be prevented from entering along the chuck shaft 31 into the interior of the extension 22. Thus, in the embodiment shown, the groove in the upper portion of the chuck shaft 31 is provided with a suitable seal, such as O-ring 32 to bear against the interior surface of the sleeve 25 and effect a seal thereagainst while allowing horizontal pivoting of the chuck 11. Similarly, at the bottom of the shaft 31 the closed end bushing 27 prevents entry of foreign material past the bottom of the shaft into the interior of the extension 22.

The assembly of the extension 22 on the handpiece housing 13 and the location of the bearing 16 and shaft 15, as well as the remaining components of the handpiece, can be conventional and requires no further comment.

A family of different blades can be used with a given chuck as long as the mounting portions 123 of all the blades conform to the dimensions of the chuck slot 55 and locking spindle 105 therein. For example, blades may differ in thickness, even in the mounting portion 123, as long as the blade thickness in the mounting portion 123 does not exceed the effective height of the slot 55. In one chuck embodying the invention, blade thickness was in the range of 0.025 inch to 0.050 inch. The recess 83 in the bottom member 51 is preferably deep enough to allow the ramps 93 to be pushed down flush with the top 87 of the shoe cover 86 and the top face 80 of the bottom member 51, i.e. with the bottom of the slot 55.

Further, blades may differ in plan, as to both shape and size in their portions outside the chuck, but with their mounting portions 123 being substantially the same.

A blade 12 is fixed in the chuck as follows. The mounting portion 123 of the blade is pushed rearward into the chuck slot 55.

Initial entry of the blade into the chuck slot 55 is made easy by the fact that the first entering portion of the blade, namely the nose 120 is small in height and width compared to the chuck slot 55 which it is to enter. Thus, the nose 120 initially guides the blade 12 easily into the slot 55. Thereafter, the wider rear end 125 of the blade 12 enters the slot 55. This entry is aided by the rounded corners 128 at the rear end 125 of the blade and by the beveled edges 65 at the front end of the slot 55.

Rearward travel of the blade 12 is positively stopped when the blade is only partway (here about halfway) into the chuck, due to collision of the rear end of the nose 120 with the locking segment 109 of the spindle 105 (as seen in FIG. 5A). The locking segment 109 is of diameter greater than the width of the blade mouth 131 and so positively blocks further entry of the blade 12 into the chuck 11. In this position, the blade 12 is quite loose in the chuck 11, and can pivot with respect to the chuck horizontally and vertically (can yaw and pitch). By far the greater portion of the mass of the blade 12 is outside the chuck. The blade 12 very easily falls out of the chuck 11 in normal handling of the handpiece 10, if by operator error the blade is left in its FIG. 5A position. Thus it will be obvious to the operator handling the handpiece that the blade 12 is not chucked, and that complete chucking will require further action by the operator. The blade 12 would normally fall out of its FIG. 5A position in the chuck in normal handling before the handpiece 10 is positioned for use at a surgical site and hence before it is likely that the trigger T would be pulled by the operator. If the trigger T (FIG. 2) is pulled accidentally with the blade 12 in its FIG. 5A position, the resulting motion of the chuck will tend simply to cause the blade to fall out of the chuck and not cause the chuck to throw the blade.

To insert the blade 12 beyond its FIG. 5A position, the operator must depress the spindle 105, from its FIG. 4A position, by downward finger or thumb pressure on the top of the head 106, preferably downward beyond its FIG. 4 position so that the top of the locking segment 109 is flush with or somewhat below the top wall 87 of the shoe cover 86. In this way, the wide locking segment 109 is out of the way of the nose 120 of the blade. The mouth 131 is wide enough to accept the unlocking segment 108 of the spindle, allowing the blade to be pushed to its FIG. 5C position. The distance the blade travels from its FIG. 5A position to its FIG. 5C position is small and is approximately the diameter of the locking segment 109.

If the operator accidentally releases the locking spindle 105 at this time, the spring 114 will immediately raise the locking spindle 105 up through its FIG. 4 position to its uppermost FIG. 4A position, causing the locking segment 109 to lodge in the rear circular part 133 of the slit 127 as shown in FIG. 5C. This positively locks the blade 12 in the chuck 11 and positively prevents any inadvertent release of the blade 12 from the chuck 11 despite actuation of the handpiece 10, violent jerking of the handpiece 10, etc. Thus, by its very short travel from its FIG. 5A position to its FIG. 5C position, the blade 12 is taken from a condition where it will fall freely out of the chuck 11 without harm, to a condition in which it is positively locked within the chuck. The FIG. 5C position may thus be termed a safety, or safety locking position because the blade cannot be accidentally removed from the chuck although it is not yet in a position of use within the chuck. The blade may thus be said to have a safety locking portion comprising the slit part 133. In the FIG. 5C position, the blade can pitch freely up and down with respect to the chuck, which will make apparent to an operator that the blade 12 is still not fully chucked.

Normally the operator maintains the locking spindle head 106 depressed below its FIG. 4 position all during insertion of the blade 12 into the chuck. Thus, the blade would normally pass through its FIGS. 5A, 5B and 5D position into its fully installed FIG. 5E position without the above discussed stopping in its FIG. 5C position.

More particularly, then, continued insertion of the blade 12 into the chuck 11 with the locking spindle head 106 fully depressed, allows the blade to continue through its FIG. 5D position wherein the unlocking segment 108 passes through the neck 134 as shown in FIG. 5D and into the front circular part 132 of the slit 127, bringing the blade to its fully installed position of FIG. 5E. Collision of the blade rear end 125 with the depending pins 63 clearly tells the operator that the blade 12 is fully inserted in the chuck 11 and the operator can release the locking spindle head 106.

Even if the operator prematurely releases the locking spindle head 106, with the blade 12 in its FIG. 5D position, the top of the locking segment 109 of the spindle 105 will simply ride on the underside of the blade 12 until the locking spindle enters the front circular part 132 of the slit 127, whereupon the spring 114 drives the locking spindle 105 upward and thereby raise the spindle locking segment 109 up into the circular front part 132 of the slit 127, as shown in FIG. 5E. The blade is thus fully installed within the chuck.

In its fully installed, or final locking FIG. 5E position, the blade rear end 125 firmly abuts the depending pins 63 of the chuck top member 50 to positively prevent further entry into the chuck while eliminating any significant rearward stress on the locking spindle 105 during cutting. The blade may thus be said to have a final locking portion comprising the slit part 132. The side edges 124 of the blade abut substantially more than half the entire length of the side walls 62 of the groove 55, which positively prevents significant yawing of the blade with respect to the chuck during operation and without placing high unit pressures on blade edges 124.

Figure 4C:
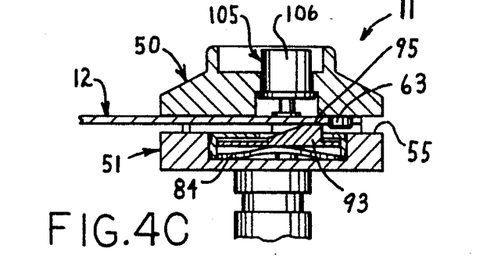
Figure 8:
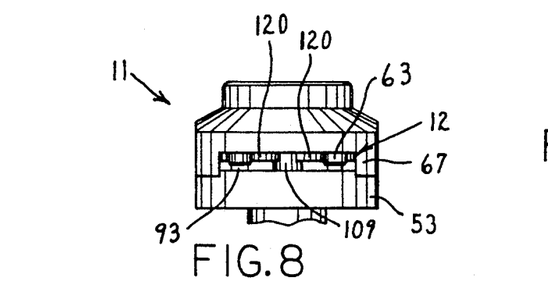
FIG. 8 is an enlarged rear elevational view of the chuck substantially as taken on the line 8—8 of FIG. 3, with a blade inserted.

The rear end 125 of the rearward moving blade 12, after passing its safety position of FIG. 5C, rides up the slopes 194 of the ramps 193 (FIGS. 4B and 5D) and is thereby pushed up against the top 61 of the slot 55 of the chuck 11. The rear end 125 of the blade continues further rearwardly along the slopes 94 of the ramps 93, depressing the ramps 93 against the force of the wave spring 84, as seen in the transition from FIG. 4B to FIG. 4C. Further insertion of the blade 12 causes it to cover the tops 95 of the ramps 93 (FIGS. 4C and 5E). The wave spring 84 acts strongly enough through the tops 95 of the ramps 93 to firmly hold the parts of the blade 12 to the rear (the nose 120 and rear end 125) and front thereof, and hence the entire chucked mounting portion 123 of the blade 12, flat against the top 61 of the slot 55 of the chuck 11 (FIGS. 4A, 4C and 8). The thus fully chucked blade 12 thus strongly resists any tendency to pitch, with respect to the chuck 11, during use.

Forward withdrawal of the blade 12 from the chuck 11, after use, is by a reversal of the above steps required to chuck the blade. More particularly and briefly stated, the operator applies his thumb or forefinger to the top of the spindle head 106 to push same from its FIG. 4A position downward past its FIG. 4 position to disengage the locking portion 109 from the spindle from the blade 12. The operator can simply then pull the blade 12 forward out of the chuck 11. Thereafter, the operator can release the spindle 105, allowing it to rise back to its FIG. 4A position.

The chuck 11 is able to chuck blades of a range of thicknesses, for example, at least twice as thick as the blade 12 here shown, and if desired a somewhat thinner blade than the blade 12 here shown. For example, one set of blades constructed according to the invention ranged in thickness from about 0.025 inch to about 0.05 inch with the height of the slot 55 being about 0.055 inch.

Figure 3:
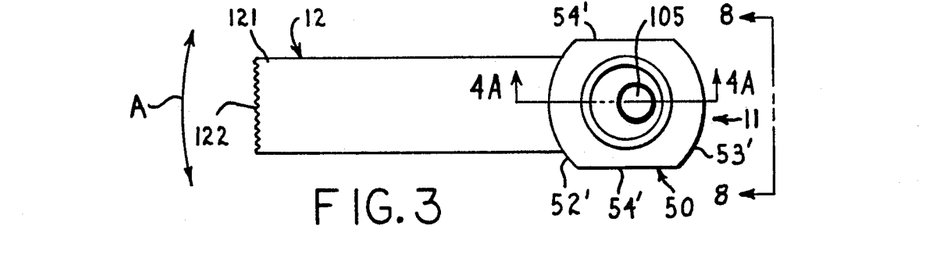
FIG. 3 is a top view of the chuck and blade structure of FIG. 2.

With a blade 12 installed in the chuck 11, the handpiece 10 can be actuated conventionally to produce the desired oscillating or sagittal motion of the chuck and hence of the blade teeth, such motion being schematically indicated by the arrow A in FIG. 3. In the embodiment schematically shown in FIG. 2, pressing of the trigger T by the operator causes the switch S to apply power from the power source P to the motor M to rotate the shaft 15 and orbit the eccentric drive pin 20 and thereby laterally swing the link 35 back and forth horizontally to cause a small arcuate oscillation in a horizontal plane of the chuck 11 and blade 12.

The lateral swing of the saw blade 12 is typically in the range of 3 degrees to 6 degrees, for example, 4.5 degrees.

Thus, the invention, as can be seen from the foregoing, provides several advantageous results. These include the following.

The chuck 11 has only a single slot 55 opening to the outside but yet can accommodate blades of differing thickness and still provide the ability to make precision cuts, such as those encountered in total knee arthroplasty.

Further, only a relatively low spring force (of the spring 114), urging the blade 12 against the "roof" (central flat 61) of the chuck, is required to eliminate excessive vibration and "play" of the blade with respect to the chuck while cutting and to allow the user of the handpiece to maintain precise control of the blade during cutting. Further, such spring force (of spring 114) is low enough that any resulting frictional forces tending to resist insertion or retraction of the blade with respect to the chuck can be readily overcome by hand.

Further, in the safety lock position (for example, see FIG. 5C) the blade 12 is positively locked in the chuck 11, although not yet fully inserted thereinto. If the blade has not been inserted far enough into the chuck to be positively locked in its FIG. 5C safety lock position, then the blade is still so loose in the chuck that it is immediately apparent that it is not chucked and it is not ready for use. Indeed, in that condition, if the chuck is angled downward, the blade will simply fall freely from it. Prior to reaching the safety lock position of FIG. 5C, there is no intermediate range of insertion in which the blade is frictionally retained sufficient to mislead a user into thinking that the blade is fully inserted or locked in the chuck or in a position of use. Well before the blade has been inserted far enough into the chuck to be in its FIG. 5E position of use, it must already have been positively locked (as in FIG. 5C) against accidental dislodgement from the chuck. The foregoing avoids a blade being forcibly thrown from the chuck upon triggering of the handpiece following a careless partial insertion of the blade.

In addition, the relative location of the locking spindle 105 and ramps 93 and the relative location of the spindle engaging rear end of the nose 120 With respect to the ramp engaging rear edge 125 of the blade prevents any significant gripping of the blade by the chuck until the blade has been inserted enough as to be in or past its FIG. 5C safety lock position.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical handpiece, a cutting apparatus comprising:
    a blade having cutting means;
    a chuck including a blade receiving slot for longitudinally slidably receiving said blade therein;
    cooperating mounting means in said chuck slot and on said blade defining safety locking means and final locking means on said chuck and blade interengageable to positively lock said blade in said chuck respectively upon a partial insertion and a full insertion of said blade into said chuck slot.

2. The apparatus of claim 1 in which said locking means of said chuck comprises an upstanding spindle vertically moveable in said chuck through said chuck slot and having vertically adjacent locking and unlocking portions respectively engageable with the blade to lock it in the chuck and unlock it from the chuck, the top of the spindle defining a head captive in and projecting upward through a hole in the top of the chuck and depressible by a human user to unlock the blade from the chuck, the top of the chuck having an upstanding fence loosely surrounding said spindle head and rising to a level near the top of the spindle head in the highest position of the latter, the highest position of the spindle being the locking position thereof, said fence being arranged to prevent inadvertent unlocking actuation of said spindle by the palm of the hand of the user while allowing intended unlocking actuation of said spindle head by the thumb or finger of the user, so as to readily permit the user to unlock the blade intentionally but tending to safeguard against inadvertent unlocking of the blade from the chuck.

3. The apparatus of claim 1 in which said locking means on said blade comprises a slit, said slit having a pair of notches longitudinally spaced along the length thereof for positively locking the blade with respect to the locking means in said chuck slot and thereby for positively locking said blade in two distinct positions in said chuck, which positions are respectively shallower and deeper in said chuck.

4. The apparatus of claim 1 in which said mounting means on said blade includes a slit in said blade, said blade having an edge and a narrow nose protruding along said edge of said blade, said slit opening through said nose, said chuck having projection means projecting into said chuck slot for abutting said edge of said blade beside said nose to determine the full insertion position of said blade in said chuck, said projection means being independent of said safety and final locking means and spaced remote from where the blade enters the slot.

5. The apparatus of claim 1 in which said chuck slot and blade each have a thickness dimension, the blade thickness being less than the chuck slot thickness, and including ramp means and spring means pressing said ramp means resiliently into said chuck slot along the thickness dimension of said chuck slot, the ramp means having a slope facing an end of said chuck slot into which the mounting means of the blade is insertable, said slope engaging an inserted blade to force same thicknesswise of the chuck slot against an opposed face of the chuck slot, said ramp means being located to underlie a blade fully inserted into said chuck slot to hold it face to face against said opposed face of the chuck slot.

6. A surgical handpiece, a cutting apparatus comprising:
    a blade having first and second edge portions, said blade having cutting means at said first edge portion thereof;
    a chuck including a blade receiving slot for longitudinally slidably receiving said blade therein;
    cooperating mounting means, in said chuck slot and at said second edge portion of said blade, defining safety locking means and final locking means on said chuck and blade interengageable to positively lock said blade in said chuck respectively upon a partial insertion and a full insertion of said blade into said chuck slot, said mounting means on said blade comprising a slit opening through said second edge portion of said blade,
    said slit being substantially dumbbell shaped, having an opposed safety locking pair of semi-circular notches on opposite sides of the slit adjacent to and open to the open end of said slit and further having a final locking circular aperture adjacent the other end of the slit, the safety locking pair of notches and final locking pair of notches respectively defining the safety and final locking means of said blade.

7. A surgical handpiece, a cutting apparatus comprising:
    a blade having first and second edge portions, said blade having cutting means at said first edge portion thereof;
    a chuck including a blade receiving slot for longitudinally slidably receiving said blade therein, a recess in the bottom of said chuck and communicating with said chuck slot, an inverted cup-shaped shoe cover fixed in said recess essentially flush with the bottom of said chuck slot and defining, with the bottom of said recess, a chamber, a disklike shoe and an underlying compression spring trapped in said chamber, said shoe cover having a top wall provided with longitudinally extending slots, said shoe having ramps upstanding through said slots, said ramps protruding upward into said chuck slot adjacent opposite lateral sides thereof, said compression spring pressing said ramps upward resiliently into said chuck slot, the ramps having slopes facing the front end of said chuck slot into which the rear end of the blade is insertable, said slopes engaging the rear edge of an inserted blade to force same against the top of the chuck slot, said ramps being located to underlie a blade fully inserted into said chuck slot to hold it up against the top of the chuck slot.

8. A saw blade usable in tools, particularly surgical oscillating and sagittal saws, said blade comprising:
first and second edge portions;
cutting means along said first edge portion of the blade to effect cutting upon cutting movement of the blade;
mounting means at said second edge portion of said blade, said mounting means comprising safety and final locking means for removably interlocking the blade with a chuck, said final locking means being distinct from said safety locking means,
said mounting means comprising slit means opening through said second edge portion of the blade,
said safety and final locking means comprising respective rear and front notches spaced along said slit means for sequentially receiving a projection on a chuck and therewith for locking said blade against unintended removal from such a chuck.

9. A surgical saw blade insertable in a chuck of a powered surgical handpiece, said blade comprising:
first and second edge portions;
cutting means along a first edge portion of the blade to effect cutting upon cutting movement of the blade;
mounting means at a second edge portion of said blade, said mounting means comprising safety locking means in said blade adjacent said second edge portion for locking the blade against escape at a partly inserted position in a chuck, said mounting means further comprising final locking means in said blade spaced inboard from said second edge portion for locking said blade against escape at a fully inserted position in a chuck, said final locking means being distinct from said safety locking means and being offset thereby from said blade second edge portion, said mounting means comprising an elongate slit opening through said second edge portion of the blade, said slit having a first widening intermediate its ends and adjacent said blade second edge portion for defining said safety locking means, said slit having a second widening spaced along said slit from said first widening for defining said final locking means.

10. A surgical handpiece chuck to be mounted on and driven by a surgical handpiece to produce cutting movement of a blade carried by the chuck, comprising:
means defining a blade receiving slot in said chuck, said slot opening forward for lengthwise rearward reception of an elongate blade, said chuck having opposed spaced edge walls bounding said slot, said chuck having locking means engageable with a blade received in said chuck for locking the blade in the chuck in a manually releasable manner, said slot being sized in thickness to receive blades of different thicknesses, said slot having opposed face walls spaced by said edge walls and extending transversely thereto, said face walls being adapted to face the width/length faces of a blade, one of said face walls having a recess, a shoe movably located in said recess and resiliently backed to urge same out of said recess and into said slot, shoe cover means for resiliently covering the recess to limit movement out of the shoe out of the recess, said shoe cover means having a through hole and said shoe having a ramp extending through said through hole into said chuck slot for resiliently pressing a blade in said chuck slot against the opposite face wall of said chuck slot even when a blade has a thickness less than the chuck slot.

11. The apparatus of claim 10 in which the locking means includes a locking spindle, movable through the chuck slot in the thickness direction thereof and including locking and unlocking portions alternatively locatable in the chuck slot by movement of the locking spindle transversely in the thickness direction of the chuck slot, said shoe and shoe cover means having aligned through holes for receiving said spindle loosely therethrough, said shoe cover means having a pair of said through holes disposed laterally on opposite sides of said spindle, between the spindle and the edge walls of the chuck slot, said shoe having a corresponding pair of ramps for engaging a blade on opposite sides of the spindle.

12. A surgical handpiece chuck to be mounted on and driven by a surgical handpiece to produce cutting movement of a blade carried by the chuck, comprising:
means defining a blade receiving slot in said chuck, said slot opening forward for lengthwise rearward reception of an elongate blade, said chuck having opposed spaced edge walls bounding said slot, said chuck having locking means engageable with a blade received in said chuck for locking the blade in the chuck in a manually releasable manner, said chuck comprising first and second facing members held rigidly together, the first ember having a longitudinally extending groove defining the chuck slot, the groove being generally parallel sided as defined by longitudinally extending flanking bulkheads, the second member having laterally outward facing steps extending longitudinally thereof and defining depressed flats laterally outboard thereof for receiving said bulkheads therein, said steps being of height substantially less than said bulkheads, the difference in height of said steps and bulkheads defining the thickness of said slot, and means located along said flats and bulkheads for fixedly securing said flats and bulkheads together such that first and second members define a one piece chuck with said slot extending thereinto.

13. A surgical saw blade insertable in a chuck of a powered surgical handpiece, said blade comprising:
a front portion and a rear end;
cutting means along said front portion of the blade to effect cutting upon cutting movement of the blade;
mounting means adjacent the rear end of said blade, said mounting means comprising a slit opening through the rear end of the blade, said slit having edge means relieved by rear and front notches spaced longitudinally along said slit and opening into said slit for sequentially receiving a projection on a chuck, said mounting means including a narrowed nose extending rearward at said rear end of said blade, said slit laterally dividing said nose into laterally spaced tines, said nose being narrow compared to the width of said blade, said slit extending forward from said nose into the adjacent portion of said blade, longitudinally spaced rear and front notches respectively being in said nose and in said adjacent portion of said blade forward of said nose, said mounting means further comprising means for preventing yawing movement of the blade with respect to a chuck and defined by opposite side edges on said blade, means for positively stopping insertion of said blade in a chuck and defined by rear facing edges on the rear end of the blade connecting said blade side edges to said nose, said nose being substantially shorter than said means for preventing yawing movement.

14. A surgical handpiece chuck to be mounted on and driven by a surgical handpiece to produce cutting movement of a blade carried by the chuck, the chuck comprising:

means defining a blade receiving slot in said chuck, said slot opening forward for lengthwise rearward reception of an elongate blade, said chuck having locking means in said slot engageable with a safety locking portion of a blade received to a first depth in said chuck slot for safety locking a blade in the chuck in a manually releasable manner, said chuck having blade thickness compensating means in said slot engageable with a blade received to a further depth in said chuck slot for pushing a blade thicknesswise against a reference surface and thereby compensating for blade thicknesses varying over a range and means for relatively locating said locking means and thickness compensating means along the length of said chuck slot such that a blade entering the chuck slot first is safety locked against accidental escape from the chuck and only thereafter encounters said blade thickness compensating means.

15. The chuck of claim 14 in which said slot has an open front end for receiving a blade lengthwise therein, projection means near the rear end of said slot and engageable by a blade at still further depth in said slot for positively blocking further insertion of a blade in said slot, said projection means and said thickness compensating means being laterally outboard of said locking means of said chuck, said projection means being to the rear of said thickness compensating means.

16. The chuck of claim 14 in which said locking means of said chuck comprises a locking spindle mounted for movement in the chuck through the thickness dimension of the slot for presenting locking and unlocking portions of the spindle to a blade in the slot, the spindle having a head projecting through the top of the chuck and manually depressible to present the unlocking portion of the spindle to a blade for unlocking a blade from the chuck, upstanding fence means fixed on the chuck and loosely surrounding the spindle head for permitting intended thumb or finger depression of the head by a user of the handpiece while avoiding unintended depression of the head by the palm of the user.

* * * * *

UNITED STATES PATENT AND TRADEMARK OFFICE
CERTIFICATE OF CORRECTION

PATENT NO. : 5,263,972
DATED : November 23, 1993
INVENTOR(S) : James A. EVANS et al It is certified that error appears in the above-identified patent and that said Letters Patent is hereby corrected as shown below:

Column 13, line 34; delete ", a".
Column 14, line 31; delete ", a".
          line 55; delete ", a".
Column 15, line 35; change "a" to ---said---.
          line 38; change "a" to ---said---.
Column 16, line 23; change "said" (second occurrence) to ---further---.
          line 40; change "ember" to ---member---.

Signed and Sealed this

Twenty-fourth Day of May, 1994

Attest:

BRUCE LEHMAN

*Attesting Officer*      *Commissioner of Patents and Trademarks*